United States Patent
Tiwari et al.

(10) Patent No.: US 11,344,404 B2
(45) Date of Patent: May 31, 2022

(54) DISTANCE DOMINANT INTRAOCULAR LENS

(71) Applicant: Bausch & Lomb Incorporated, Rochester, NY (US)

(72) Inventors: Nivedan Tiwari, Irvine, CA (US); Krishnakumar Venkateswaran, Aliso Viejo, CA (US); Andrew William Jones, Palm Harbor, FL (US); Chun Zhan, Oldsmar, FL (US); Lorenzo Salvatori, Lutz, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 16/232,725

(22) Filed: Dec. 26, 2018

(65) Prior Publication Data
US 2019/0254810 A1 Aug. 22, 2019

Related U.S. Application Data (60) Provisional application No. 62/633,661, filed on Feb. 22, 2018.

(51) Int. Cl.
  *A61F 2/16* (2006.01)
  *G02C 7/06* (2006.01)
  *G02C 7/04* (2006.01)

(52) U.S. Cl.
  CPC .......... *A61F 2/1618* (2013.01); *A61F 2/1654* (2013.01); *G02C 7/041* (2013.01); *G02C 7/06* (2013.01); *G02C 2202/20* (2013.01)

(58) Field of Classification Search
  CPC ..... A61F 2/1618; A61F 2/1654; G02C 7/041; G02C 7/06; G02C 2202/20
  See application file for complete search history.

(56) References Cited

U.S. PATENT DOCUMENTS

| 8,535,376 B2 | 9/2013 | Altmann | |
| 2006/0098162 A1* | 5/2006 | Bandhauer | G02C 7/042 351/159.44 |

(Continued)

FOREIGN PATENT DOCUMENTS

| CN | 101422392 A | 5/2009 |
| EP | 2503962 A1 | 10/2012 |

(Continued)

OTHER PUBLICATIONS

International Search Report and Written Opinion for Patent Application PCT/US2018/067686 dated May 21, 2019.

*Primary Examiner* — Jennifer Dieterle
*Assistant Examiner* — Tiffany P Shipmon
(74) *Attorney, Agent, or Firm* — Andrew J. Anderson, Esq.; Harter Secrest & Emery LLP (57) ABSTRACT

An intraocular lens includes a base refractive structure having anterior and posterior surfaces that are shaped for producing a first optical power and a diffractive structure formed in one of the surfaces of the base refractive structure including overlapping first and second diffractive patterns over a common aperture for producing second and third optical powers. The second optical power is an uneven division of the third optical power. The first and second diffractive patterns have respective step heights that are separately varied as a function of radial distance from the optical axis over the common aperture.

14 Claims, 6 Drawing Sheets

(56) References Cited

U.S. PATENT DOCUMENTS

| | | | |
|---|---|---|---|
| 2009/0088840 A1 | 4/2009 | Simpson et al. | |
| 2010/0097569 A1* | 4/2010 | Weeber | G02C 7/042 351/159.44 |
| 2016/0216535 A1 | 7/2016 | Zhao | |
| 2017/0227789 A1* | 8/2017 | Ando | G02C 7/044 |

FOREIGN PATENT DOCUMENTS

| | | |
|---|---|---|
| EP | 2527908 A1 | 11/2012 |
| EP | 3130314 A1 | 2/2017 |

\* cited by examiner

Table B1 -- 3.1D Profile

| Zone | Zone edge radial location (mm) | Apodized step height (mm) |
|---|---|---|
| 1 | 0.593513 | 0.00131038 |
| 2 | 0.839355 | 0.00117538 |
| 3 | 1.027995 | 0.00105429 |
| 4 | 1.187027 | 0.00094568 |
| 5 | 1.327136 | 0.00084826 |
| 6 | 1.453805 | 0.00076087 |
| 7 | 1.570289 | 0.00111077 |
| 8 | 1.678709 | 0.00106814 |
| 9 | 1.780540 | 0.00102714 |
| 10 | 1.876854 | 0.00098771 |
| 11 | 1.968461 | 0.00094980 |
| 12 | 2.055990 | 0.00091335 |
| 13 | 2.139943 | 0.00087829 |
| 14 | 2.220724 | 0.00084458 |
| 15 | 2.298667 | 0.00081216 |
| 16 | 2.374053 | 0.00078098 |

FIG. 4A

Table B2 -- 1.6D Profile

| Zone | Zone edge radial location (mm) | Apodized step height (mm) |
|---|---|---|
| 1 | 0.826136 | 0.00075611 |
| 2 | 1.168332 | 0.00061249 |
| 3 | 1.430909 | 0.00049615 |
| 4 | 1.652271 | 0.00068918 |
| 5 | 1.847295 | 0.00063885 |
| 6 | 2.023611 | 0.00059219 |
| 7 | 2.185749 | 0.00054895 |
| 8 | 2.336664 | 0.00050886 |
| 9 | 2.478407 | 0.00047169 |

DISTANCE DOMINANT INTRAOCULAR LENS

TECHNICAL FIELD

This invention generally relates to multi-focal intraocular lenses and particularly such lenses with compound diffraction gratings on refractive bases with aspheric surfaces.

BACKGROUND OF THE INVENTION

Natural crystalline lenses in the human eye accommodate power variations required to support a range of focal distances from near to far (distance) vision by changing shape. Replacement of the crystalline lenses with manufactured intraocular lenses (IOLs), such as during cataract surgery, has long resulted in a loss of such accommodation for supporting a range of focusing options. Monocular IOLs require patients to choose a given focal power, such as for supporting near or far vision, and to use eyeglasses to focus at some other distance.

Multi-focal IOLs are typically designed to provide two or more annular zones that provide different optical powers, typically using refractive and/or diffractive focusing mechanisms. Each of the annular zones has a different aperture and the outer zones can be truncated by changes in pupil size. Other multi-focal IOLs form diffractive structures over the entire lens and use different diffractive orders to divide light energy into different focal powers. A base refractive lens shaped to support far vision, for example, can be combined with one or more diffractive structures to provide intermediate and near vision. Compound diffraction gratings with harmonically related features have also been used to divide light energy into different optical powers where the second order of the lower power grating matches the first order of the higher power grating to make more efficient use of the diffracted light.

SUMMARY OF INVENTION

According to an aspect of the present disclosure, a trifocal IOL is envisioned with a distance vision dominant energy distribution under low light conditions while still providing good near and intermediate vision under bright light conditions. Diffractive profiles supporting near and intermediate vision can be apodized as a function of radial distance so that as the user's pupil opens under mesopic conditions, the proportion of light directed into the optical powers supporting near and intermediate vision is reduced leaving more light directed through the optical power supporting distance vision. This increase in distance energy with reduced near/intermediate energy under mesopic conditions is expected to minimize unwanted visual effects. The increased distribution of light supporting distance vision with pupil enlargement can be drawn primarily from a reduction in the energy devoted to near vision so that the energy devoted to intermediate vision provides a transition zone between distance and near vision over the considered range of pupil enlargement.

Preferably, the diffractive profiles are superimposed on a base refractive surface, e.g., the anterior surface of the IOL, sharing a common central axis with the diffractive profiles. The opposite side refractive surface, e.g., the posterior surface, is preferably similarly centered. Together, the opposite side surfaces are fashioned with refractive curves to provide the optical power necessary to support distance vision and can also be fashioned with aspheric profiles to compensate for anticipated spherical aberration in the overall optical system of the eye. The diffractive profiles divide optical energy into additional focal powers.

The diffractive profiles can be formed by superimposing different diffractive patterns for supporting near and intermediate vision through first and second orders of diffraction while preserving distance vision through the zero diffractive order. First order diffraction through a finer pitch diffractive pattern supports the increased focusing power of near vision, and first order diffraction through a coarser pitch diffractive pattern supports the lesser focusing power of intermediate vision. However, instead of harmonically relating the two diffractive patterns so that the features of the two patterns periodically overlap, the progressive periodicities of the two patterns depart from such regularity so that the optical power contributed by the second order of the coarser pitch pattern departs slightly from the optical power contributed by the first order of the finer pitch diffractive pattern to extend the depth of focus associated with near vision. Thus, instead of using the second order of the coarser pitch diffractive pattern to contribute to the near power otherwise provided by the finer pitch diffractive pattern, the second order of the coarser pitch diffractive pattern increases the depth of focus associated with the near power.

The diffractive features of each of the two superimposed diffractive patterns preferably define annular zones separated by vertical steps with parabolic profiles or their circular approximations extending between the steps. While the two diffractive patterns are superimposed to produce a composite diffractive profile, the step heights of the two diffractive patterns can be separately adjusted in accordance with the diffraction efficiencies of the two patterns to distribute optical power in desired amounts among the near, intermediate, and far focusing options. In addition, the step heights are also preferably varied as a function of radial distance from the optical axis to vary the distributions of optical energy among the near, intermediate, and far focusing options with increasing pupil size. Two different apodization functions are preferably applied over different radial distances from the optical axis.

An intraocular lens in accordance with this disclosure includes a base refractive structure having anterior and posterior surfaces that are shaped for producing a first optical power and a diffractive structure formed in one of the surfaces of the base refractive structure including overlapping first and second diffractive patterns over a common aperture for producing second and third optical powers. The second optical power is preferably an uneven division of the third optical power.

The first optical power is preferably conveyed through zero order diffraction of the first and second diffractive patterns for forming a distance focus. The second and third optical powers are preferably conveyed through first order diffractions of the first and second diffractive patterns forming in combination with the first optical power respective intermediate and near foci. Preferably, the first and second diffractive patterns have non-harmonic periodicities so that a second order diffraction through the first diffractive pattern produces a focus that is slightly offset from the near focus for extending an effective depth of the near focus.

The first and second diffractive patterns are preferably centered about a an optical axis of the base refractive structure and have respective step heights that are separately varied as a function of radial distance from the optical axis over the common aperture. The step heights of the second diffractive pattern are preferably varied more than the step heights of the first diffractive pattern as a function of the radial distance from the optical axis. the step heights of at least one of the diffraction patterns preferably vary in a non-progressive manner The distance focus is preferably arranged to receive an increasing portion of optical energy transmitted through the common aperture as a function of the radial distance from the optical axis. The increasing portion can be derived more from a corresponding decrease in the optical energy received by the near focus than a corresponding decrease in the optical energy received by the intermediate focus.

An intraocular lens in accordance with this disclosure can also be described as having a base refractive structure with anterior and posterior surfaces that are shaped for producing a first optical power that directs incident light through a distance focus and a diffractive structure formed in one of the surfaces of the base refractive structure over a common aperture for producing second and third optical powers that in combination with the first optical power direct incident light through respective intermediate and near foci. The diffractive structure includes a first diffractive pattern for producing the second optical power through a first order diffraction and a second diffractive pattern for producing the third optical power through a first order diffraction. The first and second diffraction patterns are superimposed over the common aperture and have non-harmonic periodicities so that a second order diffraction through the first diffractive pattern extends the focal depth of the near focus.

The distance focus is preferably arranged to receive an increasing portion of optical energy transmitted through the common aperture as a function of radial distance from the optical axis. The increasing portion of the optical energy can be derived more from a corresponding decrease in the optical energy received by the near focus than a corresponding decrease in the optical energy received by the intermediate focus. The step heights of the second diffractive pattern are preferably varied more than the step heights of the first diffractive pattern as a function of the radial distance from the optical axis. The functions for defining step height can differ over different ranges of the radial distance so that the step heights of at least one of the diffraction patterns vary in a non-progressive manner with the radial distance.

DETAILED DESCRIPTION OF THE INVENTION

Figure 1:
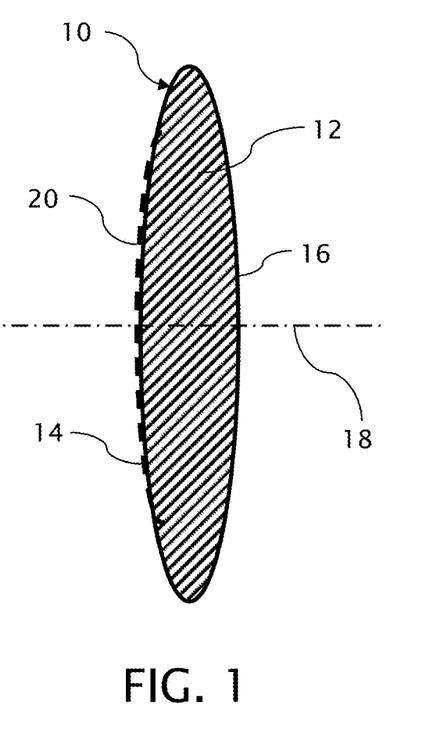
FIG. 1 is a schematic cross-section of an intraocular lens (IOL) with a diffractive profile on an anterior surface.

An intraocular lens (IOL) 10 shown in FIG. 1 has a base refractive structure 12 in a generalized form of a lens including a convex anterior surface 14 and a convex posterior surface 16 but is intended to be representative of IOLs of a variety of known forms including refractive structures with various combinations of concave, convex and planar surfaces. In addition, while the anterior and posterior surfaces 14 and 16 appear as spherical surfaces, both surfaces 14 and 16 are preferably aspheric surfaces centered about a common optical axis 18. A diffractive structure 20, which is intended to be constructed in accordance with various embodiments of this disclosure, is superimposed on the anterior surface 14 of the IOL 10 and is incorporated into the shape of the anterior surface 14.

Both the refractive profile contributed by the base refractive structure 12 and the diffractive profile contributed by the diffractive structure 20 in the anterior surface 14 are axially symmetric, and therefore, a superposition of the base refractive curve B(r) and a diffractive curve D(r), with "r" being the radial distance from optic central axis, can define the entire optical region of the anterior surface 14. The base refractive curve B(r) can be varied in accordance with other refractive parameters of the IOL 10, including the shape of the posterior surface 16 and the thickness of the base refractive structure 12, to support a range of base optical powers intended for distance vision while also incorporating an appropriate conic constant to adjust for spherical aberration.

However, for manufacturing purposes, the base refractive profile of the anterior surfaces is preferably held constant over limited ranges of optical powers and the base refractive profile of the posterior surface is varied to adjust optical power within the limited ranges. The posterior conics were developed to effect an approximately equal negative spherical aberration over the entire range of optical powers. U.S. Pat. No. 8,535,376 entitled "Aspheric Lenses and Lens Family" is hereby incorporated as a reference for fashioning a family of IOLs with a desired amount of spherical aberration.

Figure 2A:
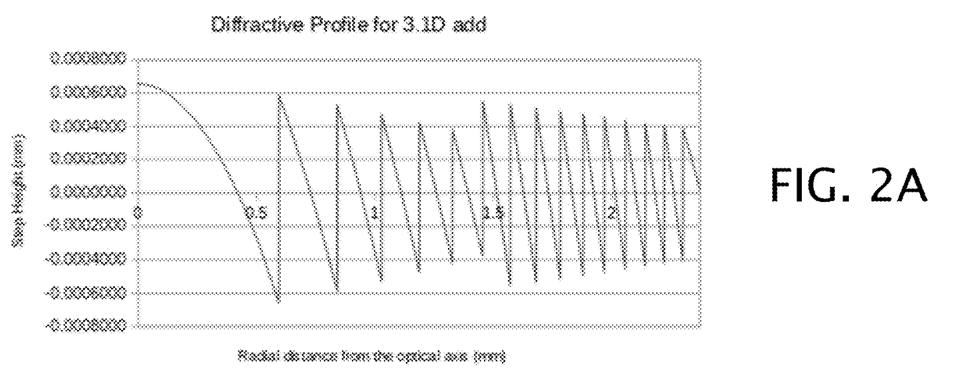
FIG. 2A plots the profile of one of two overlapping diffractive patterns for producing a near focus.
Figure 2B:
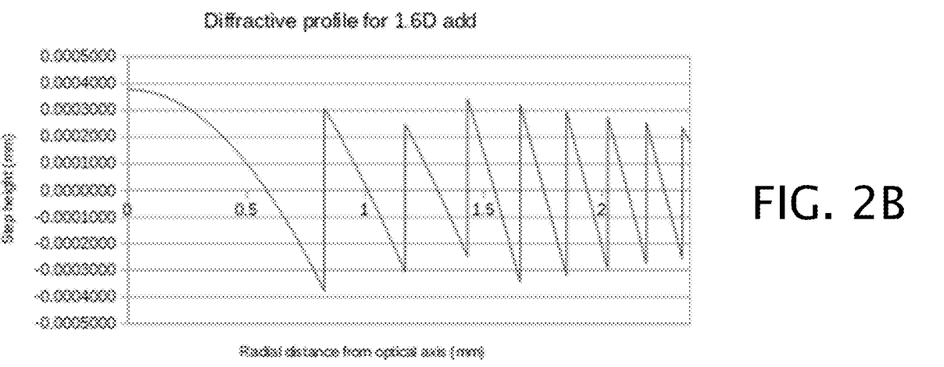
FIG. 2B plots the profile of the other of the two overlapping diffractive patterns for producing an intermediate focus.
Figure 2C:
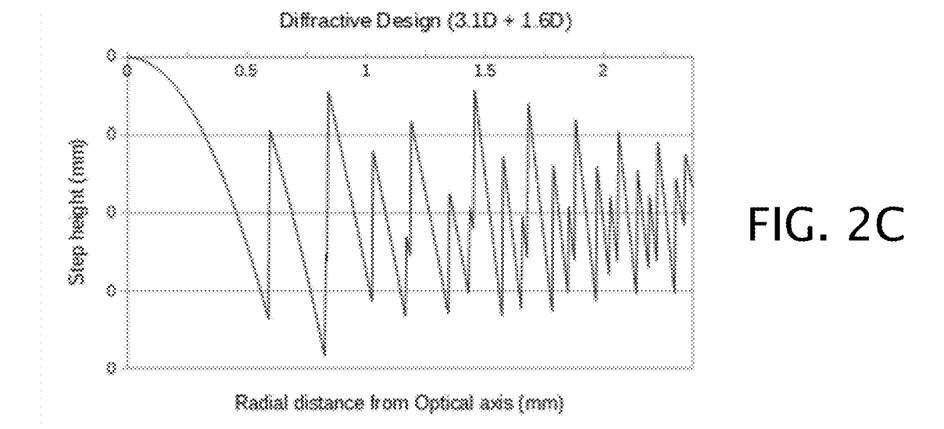
FIG. 2C plots a combined profile of the two overlapping diffractive patterns.

The diffractive structure 20 divides the optical energy passing through the IOL 10 into multiple diffraction orders that result in multiple focal zones. The zeroth diffraction order conveys the optical power of the base refractive structure 12 for the distance focus. Intermediate and near foci are provided by the first and second diffraction orders that contribute additional amounts of optical power beyond the optical power of the base refractive structure 12. The diffractive surface curve D(r) is derived from the superposition of two diffractive patterns such as shown in FIGS. 2A-2C. The patterns are plotted in step heights over a range of radial distances from the optical axis 18 (with units in millimeters). The diffractive pattern of FIG. 2A contributes 3.1 D (diopters) of additional optical power through the first diffraction order for producing the near focus, the diffractive pattern of FIG. 2B contributes 1.6 D (diopters) of additional optical power through the first diffraction order for producing the near focus. The second order of the diffractive pattern of FIG. 2B contributes 3.2 D (diopters) of additional optical power, which provides a closely spaced near focus to increase the depth of focus associated with the near power. Thus, the optical power contributed by the coarser pitch diffractive pattern of FIG. 2B is an uneven division of the optical power contributed by the finer pitch diffractive pattern of FIG. 2A. The departure from a harmonic relationship between the two diffractive patterns shown in FIGS. 2A and 2B is even more apparent when the diffractive patterns are plotted as functions of the radial distance squared such that each of the diffractive patterns have a constant pitch.

Each of the diffractive patterns for contributing 3.1 D and 1.6 D of additional optical power comprise zones separated by vertical steps with a parabolic profile between the start and end points of each zone. The radial locations of the zonal end points are given by:

$$r_p = \sqrt{2pf\gamma}$$

where "p" is the zone number, "f" is the focal length of the diffractive add power, and "γ" is the design wavelength.

Figure 3:
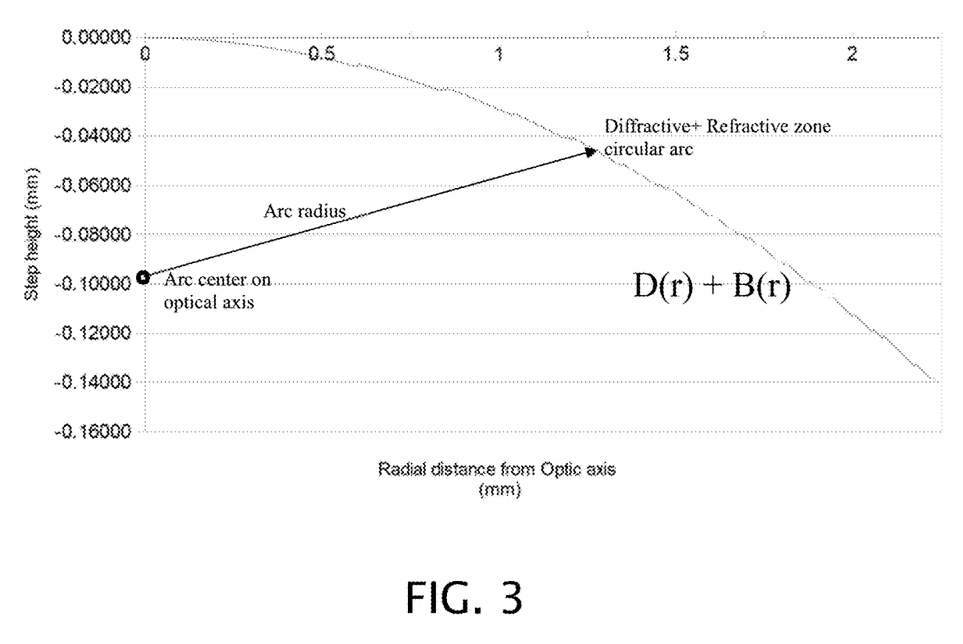
FIG. 3 plots the profile of the anterior surface of the IOL in which the diffractive profile is superimposed on the refractive profile of the base refractive surface.

The superposition of the final composite diffractive profile D(r) as shown in FIG. 2C on the base refractive curve B(r) results in a profile of the kind shown in FIG. 3. The profile is plotted in terms of step height over a range of radial distances from the optical axis 18. The diffractive profile steps apparent in FIG. 2C are about two orders of magnitude smaller than the refractive surface sag.

For purposes of achieving a distance vision dominant energy distribution under low light conditions as well as providing good near and functional intermediate vision under bright light conditions, the diffractive profile is apodized by modifying the diffractive step heights for the 3.1 D and 1.6 D patterns.

The diffractive step heights are given by:

$$h = \frac{\gamma \varepsilon}{(n_l - n_a)}$$

where, "h" is diffractive step height (unapodized); "∈" is diffraction efficiency; "γ" is design wavelength; "$n_l$" is the lens material refractive index and "$n_a$" is aqueous refractive index.

An apodization function example for the radial range $0 \leq r \leq 3$ mm is:

$$e^{-\left(\frac{r}{1.8}\right)^2}$$

An apodization function example for the radial range r>3 mm is:

$$e^{-\left(\frac{r}{3}\right)^2}$$

Figure 4A:
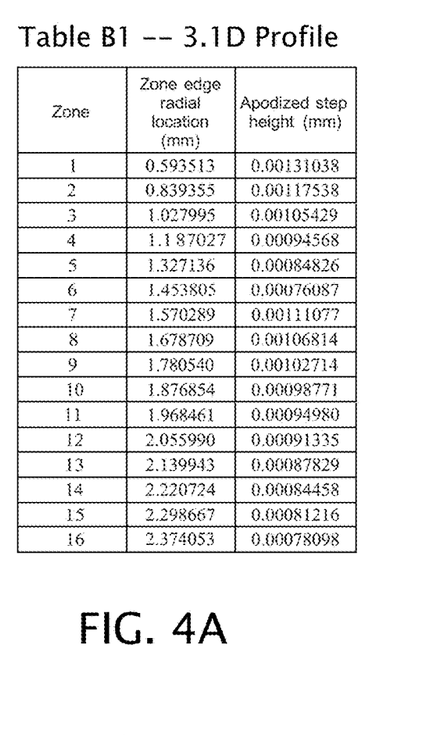
FIG. 4A contains Table B1 listing radial locations and apodized step heights of each of the zones in the diffractive pattern for producing the near focus.
Figure 4B:
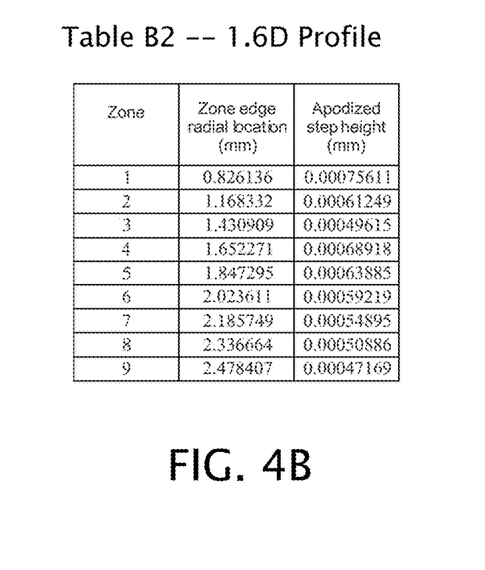
FIG. 4B contains Table B2 listing radial locations and apodized step heights of each of the zones in the diffractive pattern for producing the intermediate focus.

The resulting diffractive profile radial locations for each zone edge and apodized step height for the diffractive patterns of FIGS. 2A and 2B are listed in the respective Tables B1 and B2 of FIGS. 4A and 4B. As a result of the different functions spanning different ranges of radial distance, the apodized step heights of the two diffractive profile patterns vary in a non-progressive manner with height discontinuities appearing between the sixth and seventh zones of the 3.1 D profile and between zones three and four of the 1.6 D profile.

Figure 5:
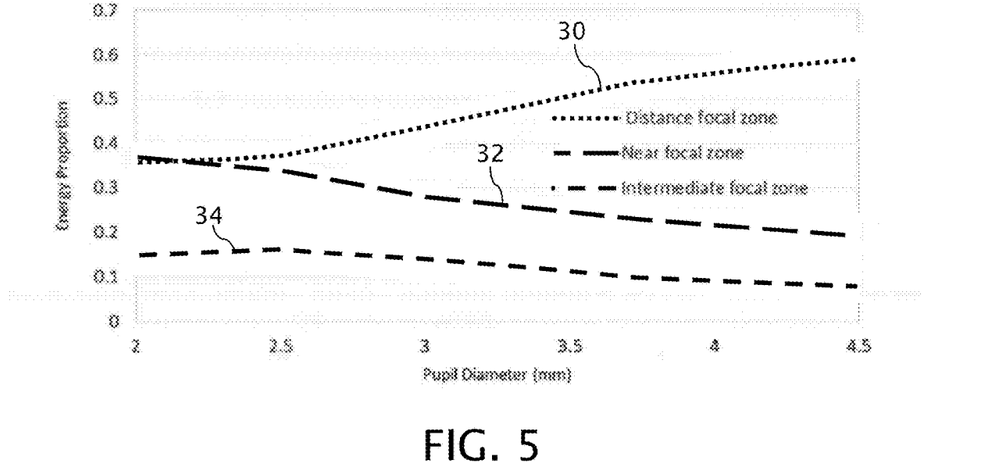
FIG. 5 plots optical energy distributions among, near, intermediate, and far (distance) focal zones over a range of pupil sizes.

FIG. 5 shows an energy balance diagram, developed using numerical simulations. Each of the three lines 30, 32 and 34 plots a respective portion of the optical energy distributed among the respective far (distance), intermediate, and near focal zones over a range of pupil diameters from 2 mm to 4.5 mm. Beginning at a pupil diameter of approximately 2 mm the portion of the optical energy delivered to the near focal zone is approximately equal to the portion of the optical energy delivered to the far focal zone but for pupil diameters from approximately 2.5 mm to 4.5 mm the portion of the optical energy delivered to the far focal zone increases while the portion of the optical energy delivered to the near focal zone decreases. The portion of the optical energy delivered to the intermediate focal zone starts at a lower level than the portions of the optical energy delivered to the near and far focal zones the pupil diameter of approximately 2 mm but declines over the range from approximately 2.5 mm to 4.5 mm pupil diameters at a shallower rate than the decline of the energy delivered to the near focal zone over the same range. Thus, most of the increase in optical energy gained by the far focal zone over the range from approximately 2.5 mm to 4.5 mm pupil diameters results from a decrease in the portion of energy delivered to the near focal zone. The intermediate focal zone provides a stable transition between the varying energy deliveries to the near and far focal zones.

Figure 6A:
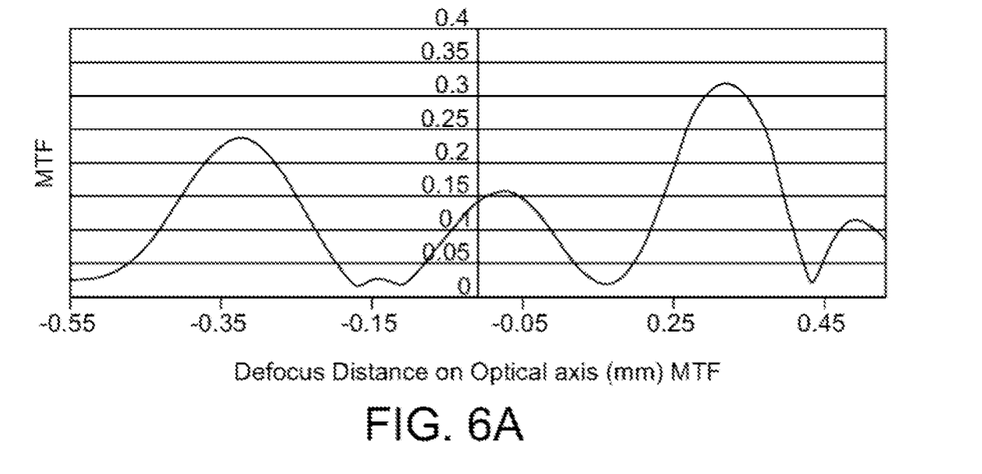
FIG. 6A plots through focus MTF values over a range of defocus distances at a 3 mm aperture.
Figure 6B:
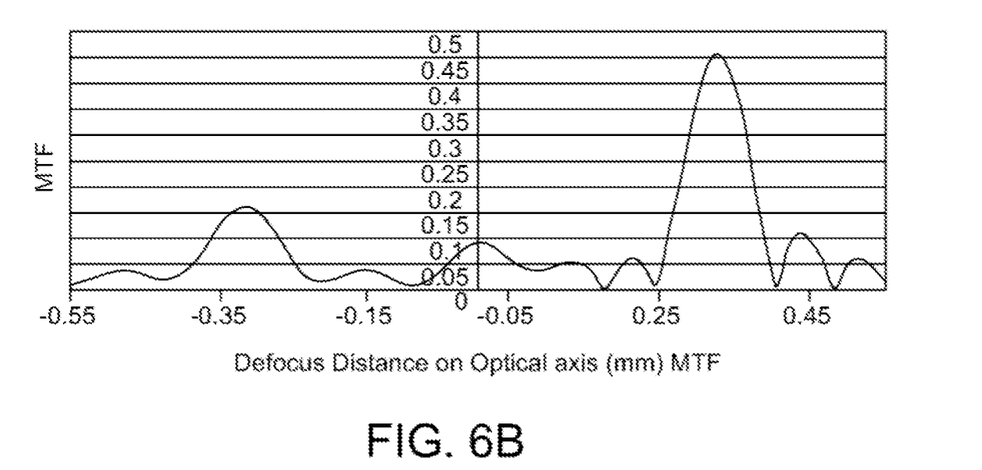
FIG. 6B plots through focus MTF values over a range of defocus distances at a 4.5 mm aperture.

Representative theoretical through focus MTF curves for a 20 D base power IOL, at 3 mm and 4.5 mm apertures, are plotted in FIGS. 6A and 6B. The MTF values are plotted over a range of positive and negative defocus distances along the optical axis. The plots contemplate a 50 lp/mm, ISO Model eye 0.15 μm SA and the IOL with −0.15 μm SA in the ISO Model Eye 1.

Figure 7A:
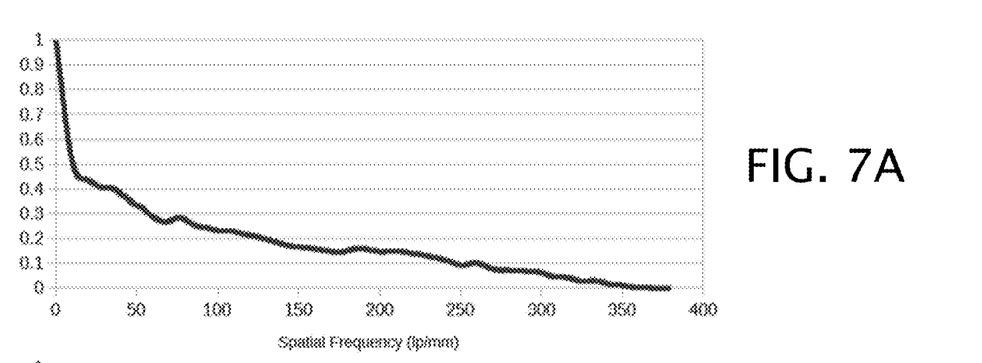
FIG. 7A plots representative theoretical through frequency MTF curves at the far focus for a 3 mm aperture.
Figure 7B:
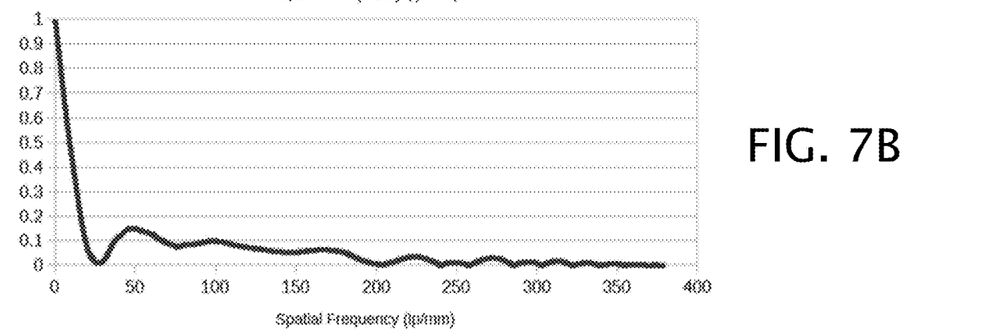
FIG. 7B plots representative theoretical through frequency MTF curves at the intermediate focus for the 3 mm aperture.
Figure 7C:
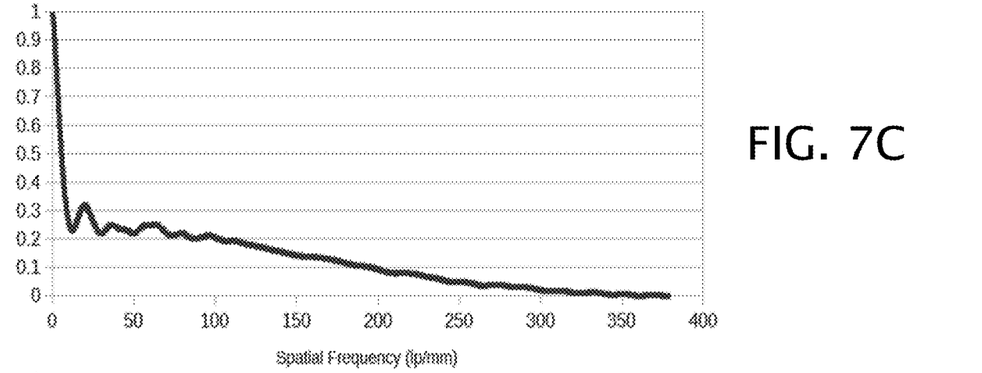
FIG. 7C plots representative theoretical through frequency MTF curves at the near focus for the 3 mm aperture.
Figure 7D:
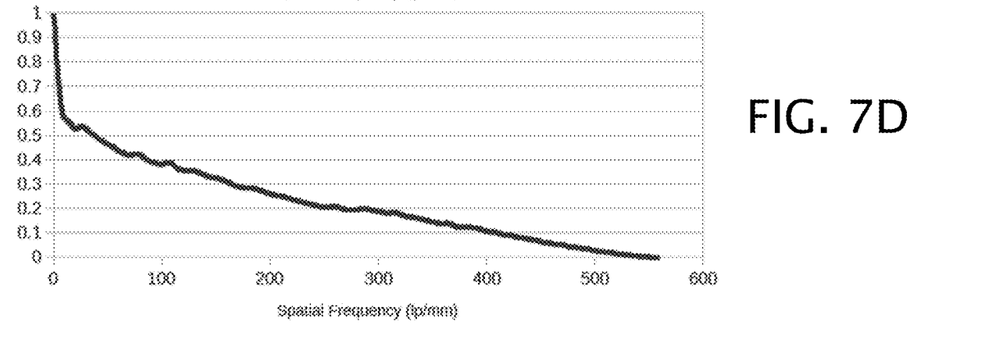
FIG. 7D plots representative theoretical through frequency MTF curves at the far focus for a 4.5 mm aperture.

Representative theoretical through frequency MTF curves for the 20 D IOL at the far (distance), intermediate, and near foci at a 3 mm aperture are respectively plotted in FIGS. 7A, 7B, and 7C. FIG. 7D similarly plots the far focus at a 4.5 mm aperture over an extended range of spatial frequencies.

The invention claimed is:

1. An intraocular lens comprising:
    a base refractive structure having anterior and posterior surfaces that are shaped for producing a first optical power;
    a diffractive structure formed in one of the surfaces of the base refractive structure including overlapping first and second diffractive patterns over a common aperture for producing second and third optical powers;
    the second optical power being an uneven division of the third optical power;
    wherein, the first and second diffractive patterns convey the first optical power through zero order diffraction for forming a distance focus,
    wherein, the first and second diffractive patterns convey the second and third optical powers through a first order diffraction for forming, in combination with the first optical power, respective intermediate and near foci, and
    wherein, the first and second diffractive patterns have non-harmonic periodicities so that a second order diffraction through the first diffractive pattern produces a focus that is offset from the near focus formed by the first order diffraction through the second diffractive pattern in combination with the first optical power for extending an effective depth of the near focus.

2. The intraocular lens of claim 1 in which:
the first and second diffractive patterns are centered about an optical axis of the base refractive structure, and
the first and second diffractive patterns have respective step heights that are separately varied as a function of radial distance from the optical axis over the common aperture.

3. The intraocular lens of claim 2 in which the step heights of the second diffractive pattern are varied more than the step heights of the first diffractive pattern as a function of the radial distance from the optical axis.

4. The intraocular lens of claim 2, in which the step heights of the second diffractive pattern are varied more than the step heights of the first diffractive pattern as a function of the radial distance from the optical axis, and wherein the step heights of the first and second diffractive patterns are configured to be separately varied such that the distance focus will receive an increasing portion of optical energy transmitted through the common aperture as a function of the radial distance from the optical axis, and so that the increasing portion will be derived more from a corresponding decrease in the optical energy received by the near focus than a corresponding decrease in the optical energy received by the intermediate focus.

5. The intraocular lens of claim 2 in which the step heights are varied as functions of their radial distance from the optical axis, and the functions differ over different ranges of the radial distance.

6. The intraocular lens of claim 5 in which the step heights of at least one of the diffraction patterns vary in a non-progressive manner with the radial distance.

7. The intraocular lens of claim 1, wherein second order diffraction through the first diffractive pattern produces a focus that is offset from the near focus formed by the first order diffraction through the second diffractive pattern by 0.1 D.

8. The intraocular lens of claim 1, wherein step heights of the first and second diffractive patterns are separately varied as a function of radial distance, and wherein two different apodization functions are applied over different radial distances from the optical axis.

9. An intraocular lens comprising:
a base refractive structure having anterior and posterior surfaces that are shaped for producing a first optical power that directs incident light through a distance focus;
a diffractive structure formed in one of the surfaces of the base refractive structure over a common aperture for producing second and third optical powers that in combination with the first optical power direct incident light through respective intermediate and near foci;
the diffractive structure including a first diffractive pattern for producing the second optical power through a first order diffraction;
the diffractive structure including a second diffractive pattern for producing the third optical power through a first order diffraction; and
the first and second diffraction patterns being superimposed over the common aperture and having non-harmonic periodicities so that a second order diffraction through the first diffractive pattern produces a focus that is offset from the near focus formed by the first order diffraction through the second diffractive pattern in combination with the first optical power for extending an effective depth of the near focus.

10. The intraocular lens of claim 9 in which:
the diffractive structure is centered about an optical axis of the base refractive structure,
the step heights of the first and second diffractive patterns are configured to be separately varied such that the distance focus will receive an increasing portion of optical energy transmitted through the common aperture as a function of radial distance from the optical axis, and
so that the increasing portion of the optical energy will be derived more from a corresponding decrease in the optical energy received by the near focus than a corresponding decrease in the optical energy received by the intermediate focus.

11. The intraocular lens of claim 10 in which:
the first and second diffractive patterns have step heights, and
the step heights of the second diffractive pattern are varied more than the step heights of the first diffractive pattern as a function of the radial distance from the optical axis.

12. The intraocular lens of claim 11 in which the step heights are varied as functions of their radial distance from the optical axis, and the functions differ over different ranges of the radial distance.

13. The intraocular lens of claim 12 in which the step heights of at least one of the diffraction patterns vary in a non-progressive manner with the radial distance.

14. The intraocular lens of claim 9 in which the second optical power contributed by the first diffractive pattern is approximately 1.6 diopters and the third optical power contributed by the second diffractive pattern is approximately 3.1 diopters.

* * * * *